United States Patent
Dai et al.

(10) Patent No.: US 8,116,843 B2
(45) Date of Patent: Feb. 14, 2012

(54) METHOD FOR AUTOMATICALLY SELECTING REGION OF INTEREST COVERING HEATED AREA

(75) Inventors: Yong Ming Dai, Shanghai (CN); Xiao Dong Zhou, Shenzhen (CN)

(73) Assignee: Siemens Aktiengesellschaft, Munich (DE)

( * ) Notice: Subject to any disclaimer, the term of this patent is extended or adjusted under 35 U.S.C. 154(b) by 823 days.

(21) Appl. No.: 12/015,104

(22) Filed: Jan. 16, 2008

(65) Prior Publication Data
US 2009/0182223 A1 Jul. 16, 2009

(30) Foreign Application Priority Data
Jan. 30, 2007 (CN) .......................... 2007 1 0063172

(51) Int. Cl.
*A61B 5/05* (2006.01)
(52) U.S. Cl. ............. 600/412; 600/410; 600/411; 601/3
(58) Field of Classification Search .................. 600/411, 600/412; 601/2–4; 382/162–172, 282
See application file for complete search history.

(56) References Cited

U.S. PATENT DOCUMENTS

| | | | |
|---|---|---|---|
| 6,618,620 B1 | 9/2003 | Freundlich et al. | |
| 7,542,793 B2 * | 6/2009 | Wu et al. | 600/412 |
| 2007/0238976 A1 * | 10/2007 | Ishihara | 600/411 |

* cited by examiner

*Primary Examiner* — Brian Casler
*Assistant Examiner* — Daniel Huntley
(74) *Attorney, Agent, or Firm* — Schiff Hardin LLP

(57) ABSTRACT

In a method for automatically selecting a region of interest covering a heated area, in the context of high intensity focused ultrasonic technology during acquisition of magnetic resonance data, phase data of a scanned area are acquired, and a heated area is identified in the scanned area according to the phase data acquired. An image is reconstructed and displayed, and in the displayed image a region of interest covering the heated area is automatically demarcated according to a predetermined size of said region of interest that covers and is larger than the heated area. The method causes the heated area to be automatically and completely included in the region of interest; and eliminates the instability of a manual selection of the region of interest.

8 Claims, 1 Drawing Sheet

METHOD FOR AUTOMATICALLY SELECTING REGION OF INTEREST COVERING HEATED AREA

BACKGROUND OF THE INVENTION

1. Field of the Invention

The present invention relates to high intensity focused ultrasonic technology, and particularly to a method for automatically selecting a region of interest for an MRI-guided high intensity focused ultrasonic system.

2. Description of the Prior Art

High Intensity Focused Ultrasonic (HIFU) is a method for curing tumors using the heating effects of ultrasonic waves that takes advantage of the excellent directivity and focusing capability of ultrasonic waves to focus low energy and low frequency ultrasonic waves outside a human body to a certain target area within (with a diameter usually less than 1 mm), and to utilize the bio-effects of the ultrasonic waves to instantaneously bring the temperature at the focus to above 65° C., which is the temperature for necrotizing cells, and to cause tissue's coagulative necrosis within said target area without damaging the surrounding normal tissues, thereby ablating the tumor non-intrusively. In addition, ultrasonic waves are not radioactive, therefore they can be used for treating a patient repeatedly, and this has become the new method of best potential developed over past few years for treating tumors.

Proton Resonance Frequency (PRF) shift thermometry is a high intensity focused ultrasonic method used under the guidance of magnetic resonance. In this method, a region of interest (ROI for short) covering the heated area is selected around the focused heated area. In the prior art, normally the region of interest is inferred and selected according to temperature variation, however, the selection is done manually instead of automatically. The technique of manually selecting the ROI has the following disadvantages:

1. Manual selection can not completely ensure that the entire heated area is included in the ROI;
2. If the selected region is too large, some unnecessary areas that should not be selected, such as a part of blood vessels and some unheated area will be included in the region of interest; and if the selected region of interest is too small, a part of the heated area will be excluded, which leads to a false result; and
3. The manual selection has poor reproducibility, the operation is time-consuming and the efficiency is low.

SUMMARY OF THE INVENTION

An object of the present invention is to provide a method for automatically selecting a region of interest covering a heated area, for accurately and quickly acquiring the region of interest in an image reconstructed in an MRI-guided high intensity focused ultrasonic system.

The above object is achieved in accordance with the present invention by a method for automatically selecting a region of interest covering a heated area for an MRI-guided high-intensity focused ultrasonic system, which performs scanning during ultrasonic heating and reconstructs an image according to the scan data acquired, including the steps of acquiring phase data of a scanned area during a scanning process, determining the heated area in the scanned area according to the phase data acquired, and demarcating, in a displayed image acquired via the image reconstruction, the region of interest covering the heated area according to a predetermined size of the region of interest that covers and is larger than the heated area.

The method of the invention can further include the step of verifying the demarcation of the region of interest according to the focus position of a focused ultrasonic sensor of the system. The verification can be accomplished by performing phase recognition to the acquired phase data and determining the heated area in the scanned area according to the results of the phase recognition.

The determination of the heated area can be accomplished by comparing the phase recognition results and determining the heated area in the scanned area according to the difference between the compared results.

An area of a negative phase value can be determined as the heated area according to the difference identified between a zero phase value and a negative phase value.

Further, the area identified as having a negative phase value as the heated area is then determined.

The demarcating can proceed by highlighting the region of interest in the image.

Further, the verification alternatively can be accomplished by determining the focus position of the focused ultrasonic sensor in the image, and assessing whether the focus position is within the demarcated region of interest, and if yes, the verification is affirmative, otherwise the verification has failed.

Compared with the prior art, the inventive method has the following advantages.

The heated area is completely included in the region of interest automatically.

The instability of manually selecting the region of interest is eliminated.

The efficiency and accuracy in selecting the region of interest is improved and the method provides for automatic parameter-free selection of the region of interest.

DESCRIPTION OF THE PREFERRED EMBODIMENTS

Conventionally, a region of interest ROI has been determined by predetermining a parameter and selecting the region manually, and then setting a phase recognition mechanism to distinguish the phase of the heated area from that of the unheated area so as to verify whether the selected region of interest includes the heated area. Currently, there is no reported procedure for automatic selection of a region of interest in an MRI-guided high intensity focused ultrasonic system.

In proton resonance frequency shift thermometry, it is relatively easy to distinguish a heated area from an unheated area because the phase data value of the heated area is lower than the phase data value of the unheated area. Together with the two known factors of the focal length and the focus shape of the high intensity focused ultrasonic sensor, it is relatively easy to automatically locate the heated area without the need of setting any associated parameter.

By the use of phase recognition (also referred to as phase labeling) and the focal position of the focused ultrasonic sensor, the heated area can be identified, thereby achieving the selection of the region of interest automatically.

The entire process of the phase recognition is completed within the magnetic resonance data acquisition. The magnetic resonance data are acquired during the ultrasonic heating, and at the same time the phase data are acquired automatically; and data processing is carried out according to the acquired phase data, i.e. to carry out the image reconstruction, so as to acquire the image finally seen by a user. During this process, the phase recognition can be performed according to the acquired phase data, and the recognition algorithm needs only to add corresponding programs during the reconstruction. The reconstructed image is called a phase map. In the phase map, the phase data of unheated area is close to zero, whereas the phase data of the heated area is negative, therefore they can be easily distinguished from one another by comparison.

Figure 1:
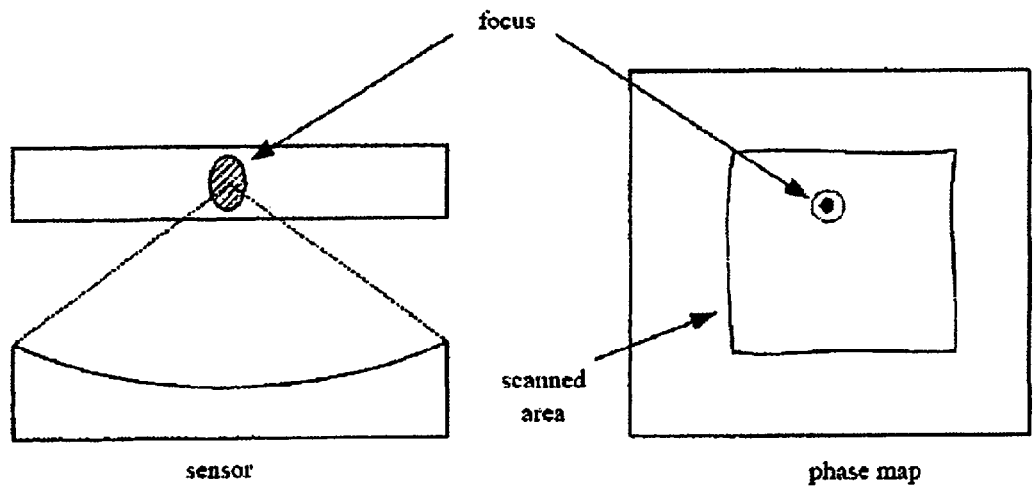
FIG. 1 schematically illustrates an embodiment for automatic selection of a heated area according to the present invention.

The focal position of the focused ultrasonic sensor has been determined according to the focal length and the shape of the focused ultrasonic sensor before heating, and has always been located in the heated area. Referring to FIG. 1, the black dot within the circle of the right-hand side phase map represents the position of the focus of the focused ultrasonic sensor in the heated area, and the left-hand side one represents the focal length and the focus shape of the focused ultrasonic sensor.

Based on above-described two conditions of phase recognition and the focal position of the focused ultrasonic sensor, the method for automatically selecting the region of interest can be realized.

The method for automatically selecting the region of interest will be further specified by the following two embodiments.

Figure 2:
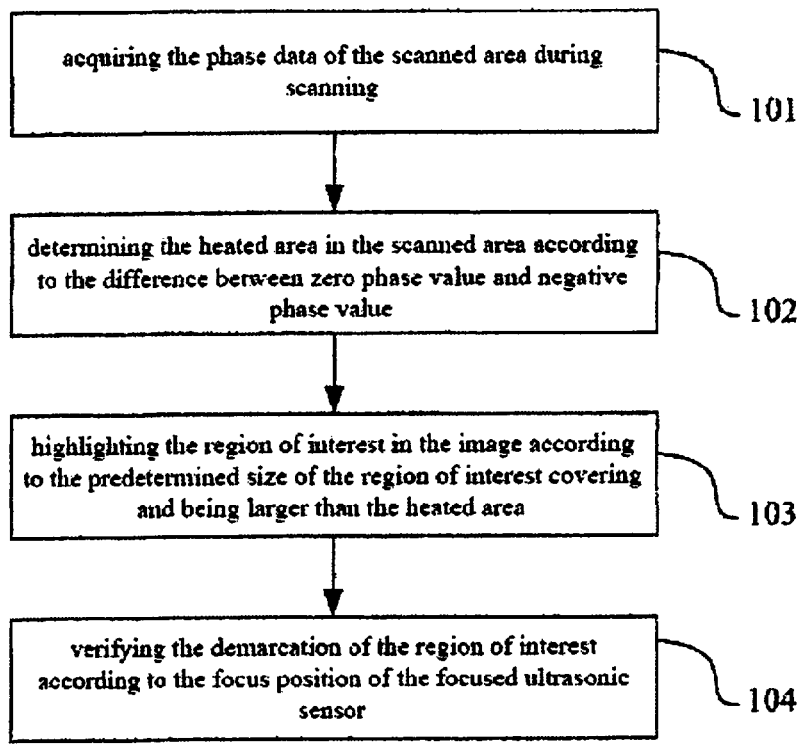
FIG. 2 is a flowchart of an embodiment according to the present invention

In the first embodiment, the heated area is determined by comparing the area in which the phase data are zero with the area in which the phase data are negative, and the complete method for automatically selecting the region of interest is shown in FIG. 2, including the steps of (101) acquiring the phase data of the scanned area during scanning and making corresponding preparation for the computation of phase recognition, and (102) performing phase recognition to the acquired phase data and determining the heated area in the scanned area according to the difference between zero phase value and negative phase value in the phase recognition results.

In the image obtained by reconstruction, the phase data of the unheated area is close to zero, whereas the phase data of the heated area is negative, so the two can be easily distinguished from each other; and based on this, the area in which the phase data are negative is regarded as the heated area and the area in which the phase data are zero is regarded as the unheated area.

In step (103) the displayed image obtained by the image reconstruction, the region of interest is highlighted according to the predetermined size of the region of interest that covers and is larger than the heated area. For example, by using a display method of highlighting the edge, such as by a yellow or green loop, the region of interest selected is demarcated in the displayed image. The predetermined size for covering the heated area can be selected according to a practical situation: for example, it can be of a large size during a certain tumor therapy, the edge of the region of interest covering the heated area may be wider than that of the heated area by several centimeters, whereas during some other tumor therapy the edge of the region of interest can be wider than that of the heated area only by several millimeters or even several microns.

In step (104) the demarcation of the region of interest is verified according to the focus position of the focused ultrasonic sensor. First, the focus position of the focused ultrasonic sensor is determined in the image; then it is decided whether the focus position is located in the demarcated region of interest. If yes, the verification is affirmative, otherwise the verification has failed. The focus position of the focused ultrasonic sensor can be determined according to its focal length and focus shape.

In the second embodiment, the area in which the phase data are negative in the scanned area is determined directly as the heated area, and except for this, other steps are the same as those in the first embodiment. The steps of the complete method for automatically selecting the region of interest are as follows.

In step (201) the phase data of the scanned area are acquired during scanning and corresponding preparation is made for the computation of phase recognition.

In step (202) phase recognition is applied to the acquired phase data, and according to the phase recognition results determining the area in which the phase data are negative as heated area.

In step (203) the region of interest is highlighted in the reconstructed display image according to the predetermined size of the region of interest that covers and is larger than the heated area.

In step (204) the demarcation of the region of interest is verified according to the focus position of the focused ultrasonic sensor.

More accurate selection results of the region of interest ROI can be realized by using the method according to the present invention. Since during the magnetic resonance, the whole heated area is initially demarcated as the ROI; then it is determined whether the focus position locates in the demarcated ROI, if the focus of sensor is located in the demarcated ROI, it indicates that the ROI includes the heated area and can be considered as the correct ROI; if the sensor focus is not located in the demarcated ROI, it indicates that the ROI is demarcated by mishandling and it is not a real ROI therefore it should be removed from the demarcated ROI. It can be seen therefrom that, the whole of the heated area is included automatically in the region of interest ROI, and at the same time, the instability of manually selecting the region of interest is eliminated, the efficiency and accuracy of selecting the region of interest are thereby improved and a basis for automatic realization of a parameter-free selection method is provided.

Although the exemplary embodiments of the present invention are described above with reference to the accompanying drawings, it should be understood that the present invention is not limited to the above particular embodiments and other variations or adaptive modifications can be made by those skilled in the art according to the present invention without departing from the scope and spirit of the present invention.

We claim as our invention:

1. A method for automatically selecting a region of interest covering a heated area in an MRI-guided high-intensity focused ultrasound system, said method comprising the steps of:

operating a magnetic resonance data acquisition unit to implement a single acquisition of phase data of a scanned area of a subject while ultrasonically heating an area of the subject, to produce a heated area within the scanned area;

providing the acquired phase data, acquired in said single acquisition, to a computerized processor and, in said processor, automatically identifying the heated area within the scanned area from the acquired phase data acquired in said single acquisition; and in said processor, automatically reconstructing an image from said phase data and from said processor, displaying said image on a display, as a displayed image, and in said displayed image, automatically demarcating a region of interest covering the heated area, identified from acquired phase data acquired in said single acquisition, according to a predetermined size of said region of interest that covers and is larger than said heated area.

2. A method as claimed in claim 1 comprising, in said processor, verifying demarcation of said region of interest dependent on a focus position of a focused ultrasound sensor of said system that is used to ultrasonically heat said heated area.

3. A method as claimed in claim 2 comprising determining the focus position of said focused ultrasound sensor in the displayed image and, in said processor, automatically assessing whether said focus position is within the demarcated region of interest and, if so, generating an affirmative verification result as an output from said processor and otherwise generating a failed verification result as an output from said processor.

4. A method as claimed in claim 1 comprising, in said processor, verifying the demarcation of said region of interest by applying phase recognition to the acquired phase data, acquired in said single acquisition, to obtain phase recognition results, and determining the heated area within the scanned area from the phase recognition results.

5. A method as claimed in claim 4 comprising, in said processor, comparing said phase recognition results and determining the heated area within the scanned area dependent on a difference among said phase recognition results.

6. A method as claimed in claim 5 comprising, in said processor, determining an area represented by a negative phase value as said heated area from a difference identified between a zero phase value and a negative phase value.

7. A method as claimed in claim 4 comprising, in said processor, determining, as said heated area, an area identified as having a negative phase value.

8. A method as claimed in claim 1 comprising demarcating said region of interest in said displayed image by automatically highlighting said region of interest in said displayed image.

* * * * *